(12) United States Patent
Gransæther et al.

(10) Patent No.: US 10,107,721 B2
(45) Date of Patent: Oct. 23, 2018

(54) FLUID SAMPLING ASSEMBLY AND METHOD OF TAKING A FLUID SAMPLE

(71) Applicant: Mirmorax AS, Stavanger (NO)

(72) Inventors: Eivind S. Gransæther, Stavanger (NO); Fredrik Lund, Trondheim (NO)

(73) Assignee: Mirmorax AS, Stavanger (NO)

( * ) Notice: Subject to any disclaimer, the term of this patent is extended or adjusted under 35 U.S.C. 154(b) by 353 days.

(21) Appl. No.: 14/787,821

(22) PCT Filed: Apr. 28, 2014

(86) PCT No.: PCT/NO2014/050066
§ 371 (c)(1),
(2) Date: Oct. 29, 2015

(87) PCT Pub. No.: WO2014/178724
PCT Pub. Date: Nov. 6, 2014

(65) Prior Publication Data
US 2016/0146712 A1 May 26, 2016

(30) Foreign Application Priority Data
Apr. 30, 2013 (NO) .................................. 20130592

(51) Int. Cl.
*G01N 1/20* (2006.01)
*G01N 29/02* (2006.01)
(Continued)

(52) U.S. Cl.
CPC .............. *G01N 1/2035* (2013.01); *G01N 1/20* (2013.01); *G01N 29/02* (2013.01); *G01N 29/222* (2013.01);
(Continued)

(58) Field of Classification Search
CPC .... G01N 1/2035; G01N 29/02; G01N 29/222; G01N 1/2042; G01N 9/24;
(Continued)

(56) References Cited

U.S. PATENT DOCUMENTS 3,031,890 A 5/1962 Struck
4,472,977 A 9/1984 Lynn
(Continued)

FOREIGN PATENT DOCUMENTS

EP 0101601 A1 * 8/1984 ............... G01N 1/10
WO WO-2010136448 A1 12/2010
WO WO-2011096823 A1 8/2011

*Primary Examiner* — Manish S Shah
*Assistant Examiner* — Timothy Graves
(74) *Attorney, Agent, or Firm* — Winstead PC

(57) ABSTRACT

Fluid sampling assembly (1, 2, 3, 4, 5, 6) adapted to be installed with fluid communication with a flow of a fluid to be sampled. The assembly comprises a rotating body (23) supported in a chamber (27) of a chamber housing (29). The chamber has a fluid inlet (31). The rotating body (23) comprises a sample compartment (33) with a sample compartment inlet (35). The rotating body (23) is connected to a rotation actuator (17). The sample compartment (33) is in fluid communication with the fluid inlet (31) when the rotating body (23) is in a rotational position where the sample compartment inlet (35) is aligned with the fluid inlet (31). The sample compartment (33) is enclosed by an inner wall (25) of the chamber (27) and inner walls of the sample compartment (33) when the sample compartment inlet (35) is in a position out of alignment with the fluid inlet (31).

9 Claims, 6 Drawing Sheets

(51) Int. Cl.
*G01N 29/22* (2006.01)
*G01N 33/24* (2006.01)
*E21B 49/00* (2006.01)
*G01N 1/02* (2006.01)
*G01N 9/24* (2006.01)
*G01N 33/28* (2006.01)

(52) U.S. Cl.
CPC ............... *E21B 49/00* (2013.01); *G01N 1/02* (2013.01); *G01N 1/2042* (2013.01); *G01N 9/24* (2013.01); *G01N 33/241* (2013.01); *G01N 33/2823* (2013.01); *G01N 2001/205* (2013.01); *G01N 2001/2057* (2013.01); *G01N 2291/0228* (2013.01); *G01N 2291/02818* (2013.01); *G01N 2291/045* (2013.01)

(58) Field of Classification Search
CPC ............ G01N 33/2823; G01N 33/241; G01N 2001/2057; G01N 2291/0228; G01N 2291/02818; G01N 1/20; G01N 1/02; G01N 2001/205; E21B 49/00
USPC ...................................................... 73/863.45
See application file for complete search history.

(56) References Cited

U.S. PATENT DOCUMENTS 5,052,213 A * 10/1991 Stock ................. G01N 33/4972
422/84
2014/0251689 A1 * 9/2014 Larson ................... E21B 21/08
175/48

* cited by examiner

FLUID SAMPLING ASSEMBLY AND METHOD OF TAKING A FLUID SAMPLE

The present invention relates to sampling of fluids. In particular the invention is useful for taking fluid samples from a flowing fluid without need of halting the flow. The assembly according to the invention is also useful for sampling of fluids containing micro particles.

BACKGROUND

In various fields involving processing or transport of fluids it is advantageous to perform measurements of the fluid characteristics. For instance, when transporting produced hydrocarbons through steel flowlines at the seabed, knowledge of the fluid contents may optimize the transport. The fluid may typically contain a mixture of gas and oil, along with water and solids such as micro particles. Such measurements are also conducted on shore, such as at hydrocarbon processing plants or other fluid processing facilities.

A simple solution of taking fluid sample from a flowing fluid is to open a valve controlling flow through a sample line and collecting the fluid sample in a sample bottle. Other solutions which are more complex and also automated exist.

A challenge associated with fluid sampling from a flowing fluid is to collect a representative sample. If the fluid comprises different components and possibly also both gas and liquid, care must be taken in order to collect a sample that is representative of the flowing fluid.

THE INVENTION

According to a first aspect of the present invention, a fluid sampling assembly is provided which is adapted to be installed with fluid communication with a flow of a fluid to be sampled. According to the invention, the fluid sampling assembly comprises a rotating body supported in a chamber of a chamber housing, said chamber having a fluid inlet. The rotating body comprises a sample compartment with a sample compartment inlet. The rotating body is connected to a rotation actuator. The sample compartment is in fluid communication with the fluid inlet when the rotating body is in a rotational position where the sample compartment inlet is aligned with the fluid inlet. Furthermore, the sample compartment is enclosed by an inner wall of the chamber and inner walls of the sample compartment when the sample compartment inlet is in a position out of alignment with the fluid inlet.

A position of the rotating body where the sample compartment inlet is aligned with the fluid inlet shall be construed herein as a position wherein there is fluid communication between the sample compartment inlet and the fluid inlet.

The term sampling shall herein be construed as isolating a portion of the fluid from said fluid flow.

Thus, a fluid sampling assembly is provided which is suitable for isolating or taking out a fluid portion from a fluid flow without needing to halt the said flow.

In some advantageous embodiments, a portion of the inner wall of the chamber comprises a measuring arrangement which is adapted to measure fluid characteristic. With such embodiments the fluid sampling assembly is also adapted to perform measurements of the sampled fluid. Moreover, with such a configuration it is not necessary to move the sample to a remote measuring device. Hence, measurements can be performed fast. In addition, little handling of the fluid sample before the measurements take place is necessary, a feature which will contribute in maintaining the fluid sample representative with respect of the fluid in the fluid flow.

Moreover, with such embodiments the measuring arrangement can advantageously be adapted to measure fluid characteristics of a fluid sample in the sample compartment at different vertical positions. This can take place when the rotating body is in a rotational position in which the sample compartment inlet is aligned with the measuring arrangement.

In some advantageous embodiments the sample compartment of the rotating body is in a through piston channel. In the through piston channel a reciprocating compartment piston is arranged. The compartment piston is adapted to reciprocate between respective end positions within the piston channel. In such embodiments the chamber also comprises a fluid outlet.

In such embodiments the rotating body comprises two compartments, namely one on respective sides of the piston. A sample compartment inlet is then present at the positions of each of the two ends of the piston channel. If such an embodiment comprises the measurement arrangement, as described above, the outflow of fluid from the sample compartment through the fluid outlet may be controlled by an outlet valve. A closed outlet valve could ensure proper calm conditions in the fluid sample during measurement, before the fluid sample is removed from the sample compartment by opening the outlet valve. Alternatively, the measurement arrangement can be arranged at an intermediate position in which, when a fluid sample in a sample compartment faces the measurement arrangement, the sample compartment inlet is not in fluid communication with the fluid outlet. Then, after a measuring step, the rotating body is rotated further so that the fluid sample can flow out of the fluid outlet. An outlet valve may then be omitted. However, an outlet valve would reduce the necessity of sealing, as the fluid pressure on the upstream side of the outlet valve could be substantially the same at all positions on either side of the compartment piston and on either side of the rotating body.

The embodiments including the compartment piston makes it possible to forward each sample through the fluid outlet. One may then accumulate a desired number of fluid samples, for instance in order to obtain a larger fluid sample that is representative of an average fluid flow over a certain time period.

The rotating body may comprise two sample compartments which are divided by a fixed portion of the rotating body. One can also imagine that the rotating body comprises more than two sample compartments, e.g. four sample compartments. In such an embodiment, the four sample compartments could be evenly distributed along the circumference of the rotating body. Then each sample compartment inlet would face in a direction pointing 90° away from the two adjacent sample compartment inlets.

One can also imagine that the rotating body has only one sample compartment (as for instance shown in FIG. 12 and FIG. 13).

With embodiments wherein the rotating body comprises a fixed portion that divides two or more sample compartments, or wherein the rotating body comprises only one sample compartment, fluid samples will be returned to the fluid flow after measurement.

For the embodiments described above including the chamber piston, the fluid outlet can be connected to an outlet line which is connected to a sample bottle. Thus a sample bottle can be filled with an appropriate number of fluid samples.

The sample bottle can be partitioned into a sample part and an auxiliary fluid part, between which a movable barrier piston is arranged. The auxiliary fluid part is then in fluid communication with a bottle outlet. An auxiliary fluid in the auxiliary fluid part may advantageously be an inert fluid, such as an inert gas, e.g. nitrogen. Such an inert fluid may be released to the environment or to the fluid flow.

In one embodiment involving the compartment piston described above, the fluid sampling assembly can be installed with fluid communication with said flow of fluid, and the fluid outlet can be connected to an outlet line which is in fluid communication with the fluid flow at a position downstream with respect to the fluid sampling assembly. Fluid samples will then be returned to the fluid flow after passing through the fluid sampling assembly. Since the pressure of the fluid flow will be less at the said downstream position, the fluid samples will be flown in such direction due to the pressure difference.

Advantageously the rotating body can be ball shaped. An advantage with such embodiments is that one may use parts from existing ball valves, or a ball valve design, for manufacturing of the fluid sampling assembly. As will be described in the more detailed description below, however, other shapes of the rotating body are indeed possible.

According to a second aspect of the present invention, it is provided a method of taking a fluid sample from a fluid flow by using a fluid sampling assembly which is installed with fluid communication with said flow of fluid. The method comprises turning a rotating body within a chamber housing from a position in which a sample compartment inlet of a sample compartment in the rotating body is aligned with a fluid inlet of the chamber housing, to a position in which the sample compartment inlet is not aligned with the fluid inlet, thereby encapsulating a fluid sample within said sample compartment. The fluid inlet of the chamber housing is in fluid communication with said fluid flow.

The method according to the second aspect of the invention may also comprise performing measurement of fluid characteristic on a fluid sample in a first sample compartment with a measuring arrangement, while letting fluid from the fluid flow enter a second sample compartment.

In such an embodiment, the rotating body comprises at least two sample compartments.

In another embodiment of the method according to the second aspect of the invention, the method further comprises opening an outlet valve in an outlet line, thereby letting pressure in the fluid flow move a compartment piston along a piston channel within the rotating body. In this embodiment a new fluid sample enters one sample compartment on one side of the compartment piston while a preceding fluid sample on the other side of the compartment piston leaves another sample compartment by being forced through the outlet line by said compartment piston.

In yet an embodiment of the second aspect of the invention, said method further comprises, when the rotating body is in the position in which the sample compartment inlet is not aligned with the fluid inlet, performing measurement of the fluid sample with a measuring arrangement. Then, after said measurement, turning the rotating body back to the position in which the sample compartment inlet in the sample compartment in the rotating body is aligned with the fluid inlet of the chamber housing, thereby replacing said fluid sample with a new fluid sample.

Although not restricted to such field of application, the person skilled in the art will appreciate that the fluid sampling assembly and method according to the invention is well suited for use in the field of hydrocarbon production or processing. Moreover, in addition to be applicable topside/onshore, the assembly and method are well suited for being used subsea. One reason for this, among other reasons, is that the solution is well suited for automation or operation by means of a remotely operated vehicle (ROV). Another reason is the possibility of making a closed system, wherein fluid samples are returned to the fluid flow.

EXAMPLE OF EMBODIMENT

While a general description of the invention has been given above, some more detailed examples of various embodiments are given in the following with reference to the drawings, in which FIG. 1 is a schematic view of a fluid sampling assembly arranged in association with a bend of a flow pipe guiding a fluid to be sampled;

Figure 1:
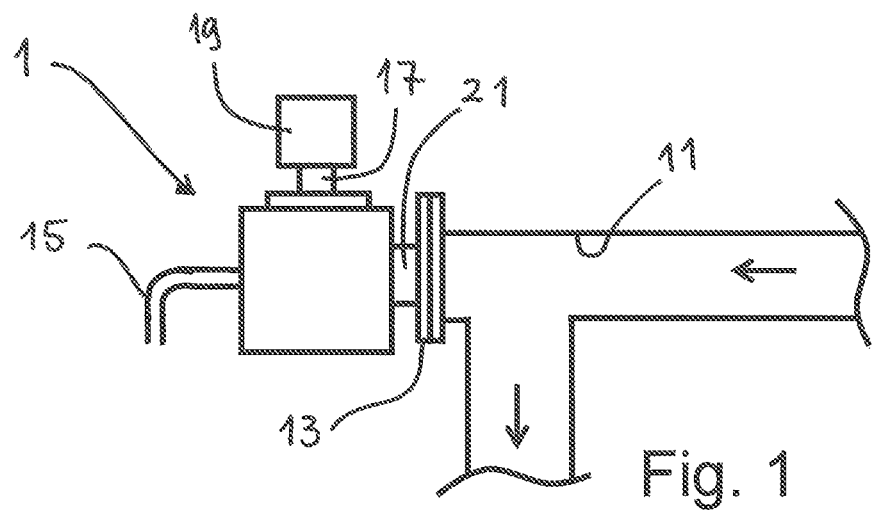

FIG. 1 shows, with a principle sketch, a fluid sampling assembly 1 according to the invention arranged in association with a flow pipe 11 that conducts a flow of fluid. The fluid sampling assembly 1 is attached to a bent portion of the flow pipe 11 by means of flanges 13, in such way that the fluid flowing in the flow pipe 11 is in fluid communication with the fluid sampling assembly 1. On a side of the fluid sampling assembly 1 which is opposite of the flanges 13, an outlet line 15 is arranged in which fluid samples may be guided. It should be noted however that in some embodiments of the fluid sampling assembly, such an outlet line 15 is not necessary. This will be appreciated from the description further below.

The fluid sampling assembly 1 comprises a rotation actuator 17, which in some embodiments may be rotated by means of an actuator motor 19. The function of the rotation actuator 17 will be described below. In lieu of an actuator motor 19, the rotation actuator 17 may be turned manually, or if arranged subsea by a remotely operated vehicle (ROV).

Figure 2:
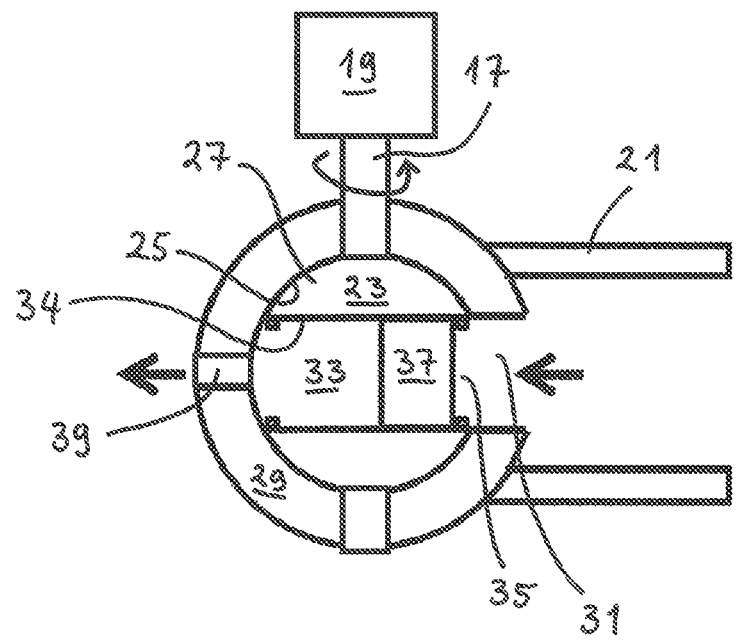
FIG. 2 is a principle side cross section view of a fluid sampling assembly according to the invention.

FIG. 2 shows a principle side view of a fluid sampling assembly 2 according to the present invention. At the right hand side of FIG. 2 is shown a pipe piece 21 which forms a fluid connection to the flanges 13 shown in FIG. 1 and thus with the fluid in the flow pipe 11. The rotation actuator 17 is connected to a rotating body 23 which in this embodiment is shaped substantially as a ball. The rotating body 23 is supported by the inner walls 25 of a chamber 27 enclosed by a chamber housing 29. As will be appreciated by the person skilled in the art, in this embodiment the rotating body 23 and chamber housing 29 resembles a ball valve in many respects. In a portion of the chamber housing 29 there is a fluid inlet 31. Within the rotating body 23 there is a sample compartment 33. When the rotating body 23 is in the shown rotational position, a sample compartment inlet 35 of the sample compartment 33 is aligned with the fluid inlet 31 of the chamber housing 29.

In the embodiment shown in FIG. 2, the sample compartment 33 is formed as a through piston channel 34 within which a reciprocating compartment piston 37 is supported. In other words, a sample compartment 33 may exist on either side of the compartment piston 37. Moreover, a fluid outlet 39 is formed in the chamber housing 29 opposite of the fluid inlet 31.

When the fluid pressure on the right hand side of the compartment piston 37, with respect to FIG. 2, is larger than the pressure on the opposite side of the compartment piston 37, the compartment piston 37 will slide towards the lower pressure side, i.e. to the left in FIG. 2. Simultaneously a sample present in the sample compartment 33 on the low pressure side will exit the sample compartment 33 and the chamber 27 through the fluid outlet 39. As this takes place, a new sample will fill the sample compartment 33 emerging on the high pressure side of the sample compartment 33.

Due to the 90° bend of the flow path at the position of the fluid sampling assembly 2, turbulence in the flowing fluid will provide a representative fluid in the sample compartment 33. As will be appreciated by the person skilled in the art, there are also other ways to provide turbulence in the flow. Moreover, for some applications a turbulent flow may not be necessary to ensure a representative fluid sample.

Figure 3:
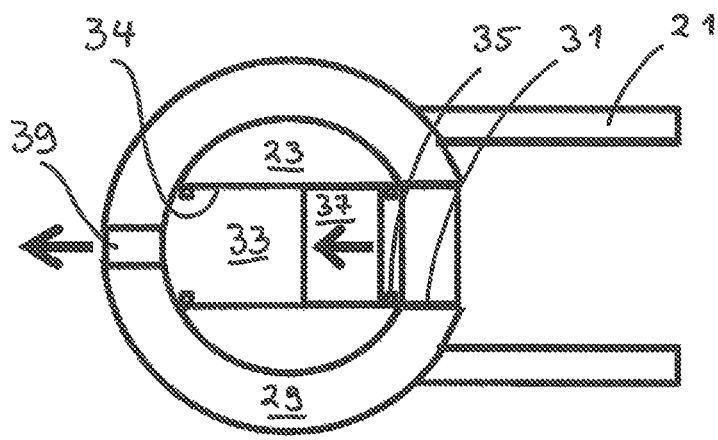
FIG. 3 to FIG. 6 are principle top cross section views of an embodiment of the invention.
Figure 4:
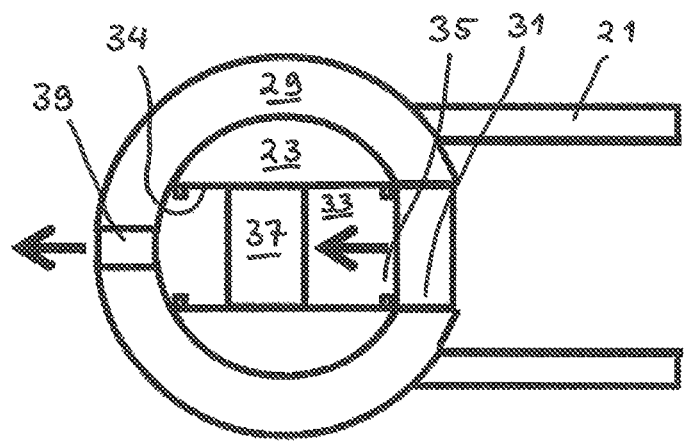
Figure 5:
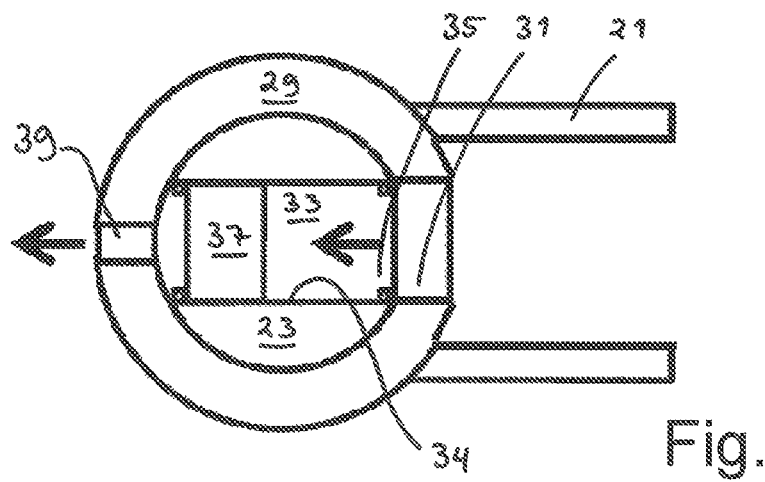

FIG. 3, FIG. 4, and FIG. 5 show top views which illustrate the motion of the compartment piston 37 and how a new fluid sample is received in the sample compartment 33. The situation shown in FIG. 3 corresponds to the one shown in the side view of FIG. 2. In this situation the compartment piston 37 has barely moved within the piston channel 34 from its end position. In the situation shown in FIG. 4, the compartment piston 37 has moved more than half the distance towards the opposite end position. In the position shown in FIG. 5 the compartment piston 37 has moved all the way to the opposite end position. In this position, the sample compartment 33 is filled with a new sample of the fluid to be sampled.

Figure 6:
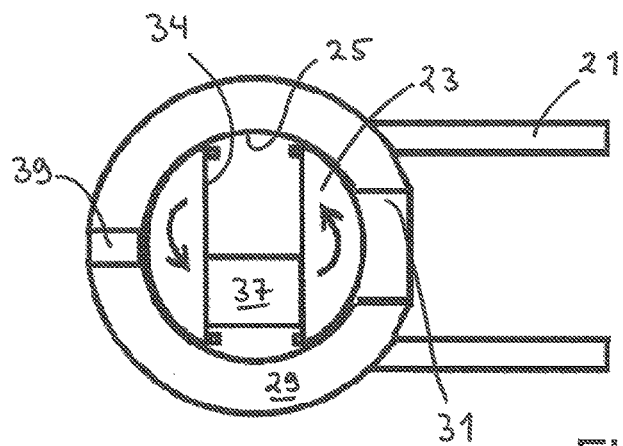

In order to isolate the new sample, the rotating body 23 is now rotated with the rotation actuator 17, which in this embodiment is a shaft extending through a portion of the chamber housing 29. The top view shown in FIG. 6 shows the rotating body 23 in a position where it has rotated 90° counterclockwise with respect of the position shown in FIG. 5. The fluid sample is now isolated in the sample compartment 33 as it is enclosed by the walls of the piston channel 34, a face of the compartment piston 37, and a portion of the inner wall 25 of the chamber 27 (or the chamber housing 29).

It will be appreciated that if the rotating body 23 continues to rotate another 90° counterclockwise, the new sample will be in fluid communication with the fluid outlet 39. Then, another new sample will start to enter the piston channel 34, again moving the compartment piston 37.

Thus, each time the rotating body 23 is rotated 180°, a new sample will be taken from the fluid flow. The configuration shown including the compartment piston 37 arranged in a piston channel 34 within the rotating body 23, makes it possible to make use of the pressure of the fluid flow to forward each sample out through the outlet line 15.

Figure 7:
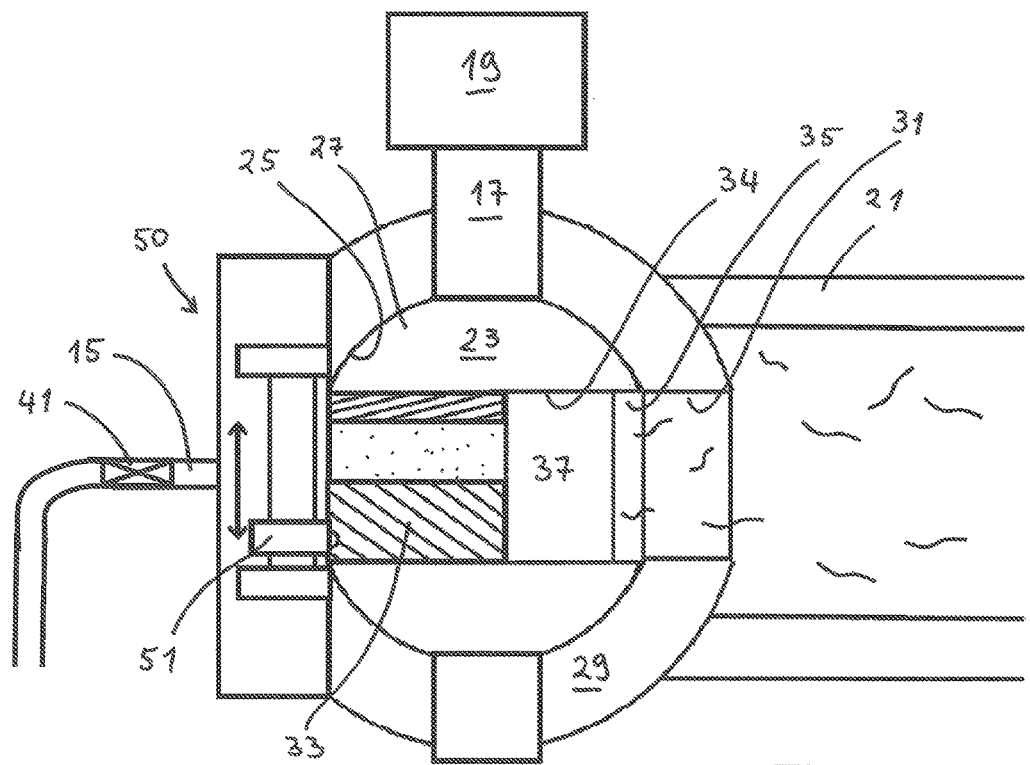
FIG. 7 is a principle side cross section view of an embodiment according to the invention during fluid characteristic measurement.

FIG. 7 is a principle side view of a fluid sampling assembly 3 according to the invention, which in many respects corresponds to the fluid sampling assembly 2 shown in FIG. 2. The fluid sampling assembly 3 shown in FIG. 7 is provided with a measuring arrangement 50. The measuring arrangement 50 forms a part of the inner wall 25 of the chamber 27 at a position which is different than the position of the fluid inlet 31. In this embodiment the measuring arrangement 50 is arranged opposite the fluid inlet 31.

When the rotating body 23 is in the position shown in FIG. 7, the fluid sample in the sample compartment 33 is adjacent the measuring arrangement 50 so that measurements of the fluid sample can be performed. As illustrated in the side view of FIG. 7, the shown fluid sample comprises at least three different components which have separated in three vertically separated layers. For a fluid flow containing hydrocarbons, such as a fluid produced from an oil or gas well, the fluid can typically comprise water, oil and gas. Water will then take the lowermost position, the oil will take the intermediated position, and gas will be on the top.

In this embodiment, the measuring arrangement 50 is provided with a measuring unit in the form of an ultrasound transducer 51 which is adapted to be moved vertically along the entire vertical extension of the fluid sample. Acoustic waves are directed horizontally into the fluid sample and reflected by the facing piston wall. The received acoustic waves are recorded and used to characterize characteristics of the fluid sample. Such characteristics may typically include density, $\rho$.

Figure 10:
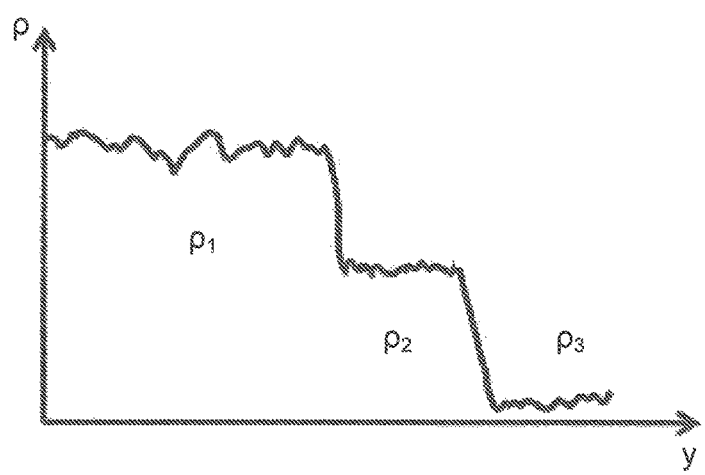
FIG. 10 is a principle view of measured density values of a fluid sample.

FIG. 10 illustrates a typical measurement result for a flow of produced well fluid comprising hydrocarbons. The diagram shows density $\rho_1$ for the water content, $\rho_2$ for the oil content, and $\rho_3$ for the gas content.

Thus, in this embodiment the measurement yields the volume of water, liquid hydrocarbons and gaseous hydrocarbons or chemicals with other properties. Furthermore, one may deduce the salinity of the water and the type of oil.

Referring again to FIG. 7, an outlet valve 41 is arranged in the outlet line 15 to control the outflow of the fluid sample in the sample compartment 33. After measuring, the outlet valve 41 is opened and the pressure on the opposite side of the compartment piston 37 moves the compartment piston 37, thereby filling a new fluid sample. When the new fluid sample is in the sample compartment 33, the outlet valve 41 is closed and the rotating body 23 is turned so that a new measurement can be made.

It is noted that the compartment piston 37 is moving freely and is only moved by the pressure drop over it. Moreover, when the outlet valve 41 is closed, the compartment piston 37 will not move and the pressure on either side of it is identical. Hence, a possible flow of fluid past the compartment piston 37 will be very small or even non-existent with an appropriate seal sealing between the compartment piston 37 and the piston channel 34.

Figure 8:
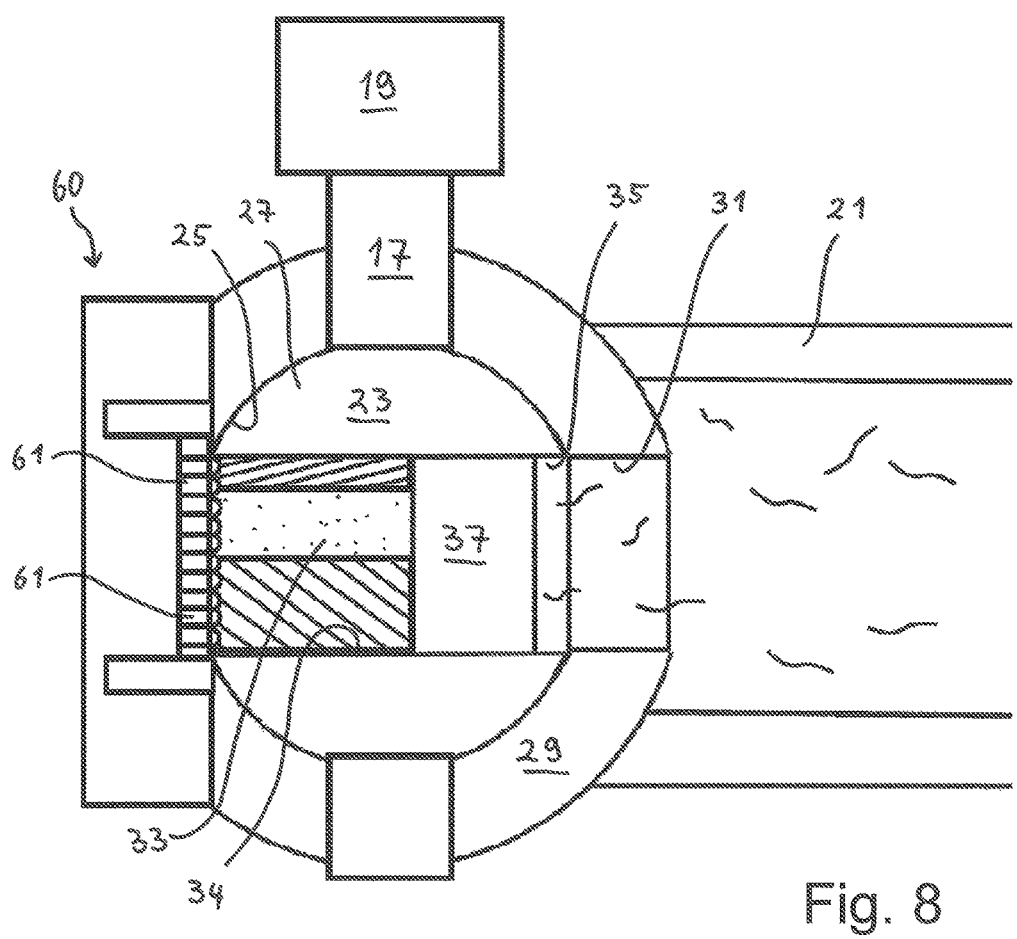
FIG. 8 is a principle view of an embodiment of the invention during fluid characteristic measurement.

FIG. 8 illustrates an embodiment of a fluid sampling assembly 4 which in many respects corresponds to the one shown in FIG. 7. In this embodiment, however, the measuring arrangement 60 is provided with an array of measuring units 61 which are vertically fixed. As will be appreciated by a person skilled in the art, in a practical embodiment a substantial larger number of measuring units 61 may be arranged in the array than what is shown in FIG. 7.

Figure 9:
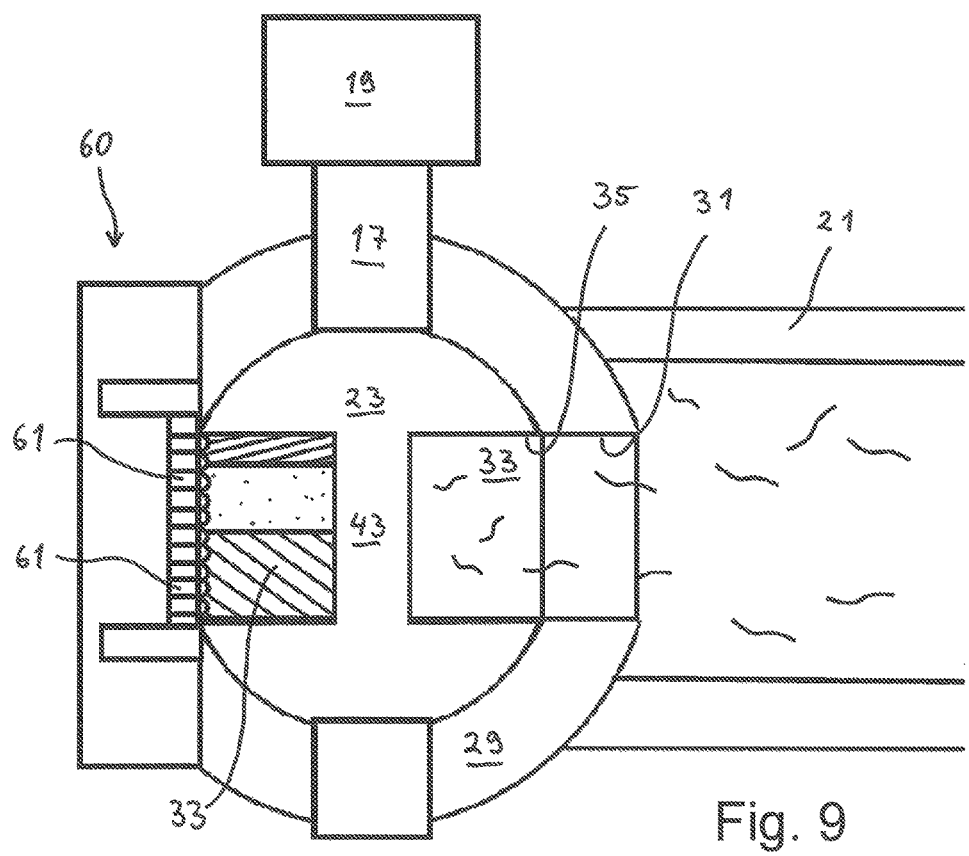
FIG. 9 is a principle view of another embodiment according to the invention.

FIG. 9 shows yet an embodiment of a fluid sampling assembly 5 according to the invention. In this embodiment the rotating body 23 is not provided with a compartment piston. In stead the rotating body 23 comprises two sample compartments 33 which are divided by a fixed portion 43 of the rotating body 23. As with the other shown embodiments, the measuring arrangement 60 is arranged opposite the fluid inlet 31. Hence, for every 180° turn of the rotating body 23, a new fluid sample will be in the position for measurement adjacent the measuring arrangement 60. The rotating body 23 shown in this embodiment has two sample compartments 33. One can, however, also imagine a rotating body 23 equipped with only one sample compartment 33, which then could be made with a larger volume. It could also have more than two sample compartments 33, for instance three or four, or even more. With the fluid sampling assembly 5 shown in FIG. 9, an outlet, such as the outlet line 15 shown in FIG. 7 is not necessary. The fluid samples which have been measured are returned directly to the fluid flow, as the current in the fluid flow will replace the measured fluid sample with a new sample.

As will be appreciated by the person skilled in the art, the embodiment of the fluid sampling assembly 5 shown in FIG. 9, is less suited than the embodiments including the compartment piston 37, if the samples shall be forwarded through an outlet, such as for filling a sample bottle.

It should also be noted that when the measuring arrangement 50, 60 is arranged as a portion of the inner wall 25 of the chamber 27, it needs not be arranged at the position which is opposite the fluid inlet 31. It may in stead be arranged at a position which is between the fluid inlet 31 and the fluid outlet 39. In such embodiments, the fluid in the sample compartment will not be in fluid communication with neither the fluid inlet 31 nor the fluid outlet 39 during measurement.

Figure 11:
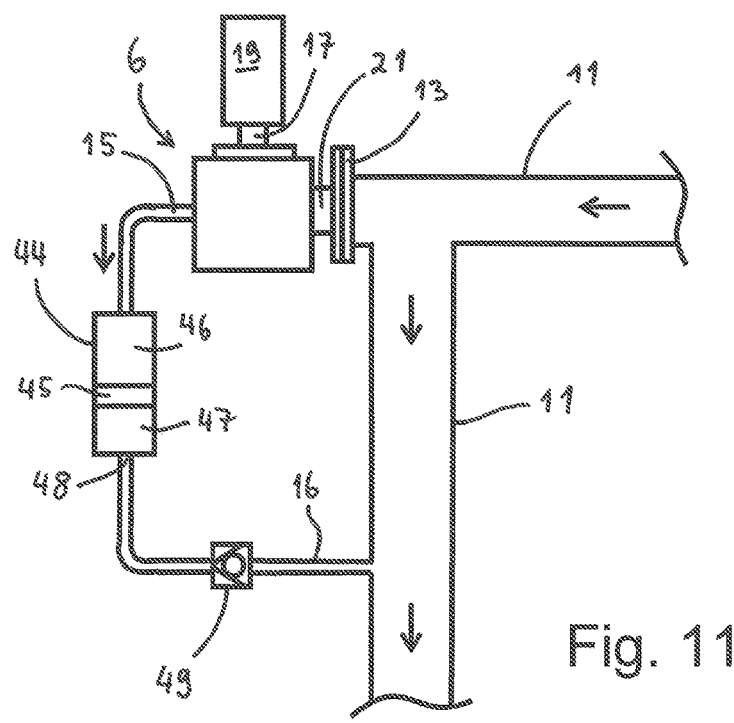
FIG. 11 is a principle view of a fluid assembly according to the invention, showing a possible configuration of the assembly together with a flow pipe guiding the fluid to be sampled.

FIG. 11 shows a fluid sampling assembly 6 according to the invention in a configuration having an outlet line 15 from the fluid sampling assembly 6 (such as the outlet line 15 shown in FIG. 7) which is connected to a sample bottle 44. The volume of the sample bottle 44 can accommodate a plurality of fluid samples leaving the sample compartment 33 through the outlet line 15.

The sample bottle 44 has inner walls which are cylindrical, and it accommodates a barrier piston 45 which constitutes a fluid barrier between a sample part 46 and an auxiliary fluid part 47 of the sample bottle 44. The barrier piston 45 can move freely inside the sample bottle 44. Hence the pressure in the plurality of fluid samples inside the sample part 46 is the same as the pressure inside an auxiliary fluid inside the auxiliary fluid part 47. Moreover, the auxiliary fluid part 47 is in communication with a bottle outlet 48. In this embodiment the bottle outlet 48 is connected to a return line 16 which leads to the flow pipe 11. The interface between the return line 16 and the flow pipe 11 is at a position where the pressure in the fluid flow is less than the pressure in the flow pipe 11 upstream of the fluid sampling assembly 6. Hence, as the sample bottle 44 is filled by fluid samples, the auxiliary fluid will enter the fluid flow in the flow pipe 11, through the return line 16. Advantageously one may arrange a check valve 49 in the return line 16. The sample bottle 44 may be removed and possibly replaced.

The auxiliary fluid may typically be an inert fluid, for instance a gas such as nitrogen, which may be inserted into the fluid flow or even into the ambience.

One may also imagine a configuration as shown in FIG. 11, however without the sample bottle 44. The outlet line 15 would then be connected directly to the return line 16, and fluid samples which have entered through the fluid sampling assembly will be returned to the flow pipe 11.

With the embodiments of the fluid sampling assembly including an outlet, one may off course perform the measuring of fluid properties at a position remote from the fluid sampling assembly. I.e. the outlet may lead the sampled fluid samples to a measuring device which is separate from the fluid sampling assembly.

Figure 12:
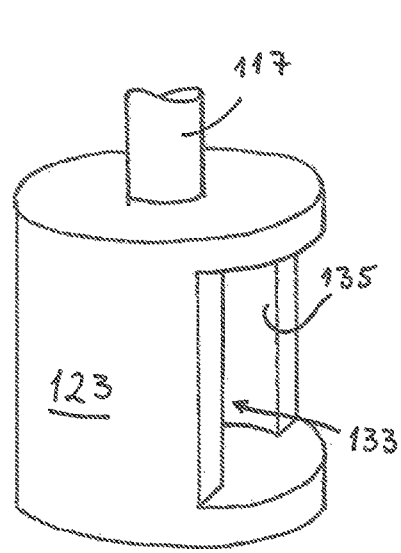
FIG. 12 is a perspective view of an embodiment of a rotating body.
Figure 13:
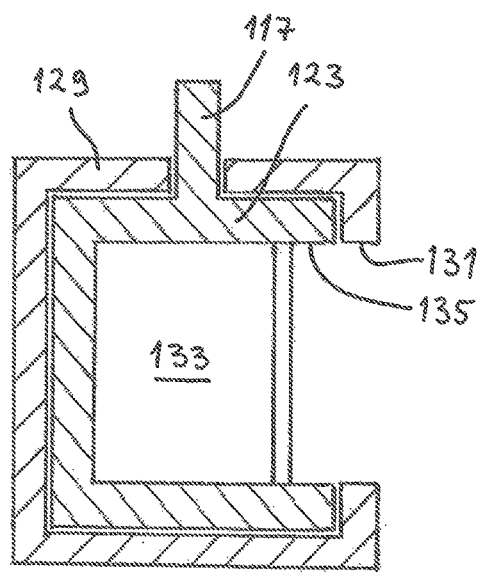
FIG. 13 is a cross section side view showing the rotating body of FIG. 12 inside a chamber.

FIG. 12 and FIG. 13 illustrate a perspective view of an alternative rotating body 123 and a cross section view of such a rotating body 123 inside an alternative chamber housing 129. In this embodiment the rotating body 123 has a main outer shape which is cylindrical and circular. It has only one sample compartment inlet 135 and can thus have a sample compartment 133 which is relatively large. To the chamber housing 129 there is arranged a measuring arrangement (not shown) and/or an outlet (not shown).

When the rotating body 123 is provided with only one sample compartment 133, it is not possible to perform measurements on a fluid sample within a sample compartment while another fluid sample is entering a second sample compartment. With embodiments such as the one shown in FIG. 9, one fluid sample can be measured with the measuring arrangement 60, while a new sample enters the opposite sample compartment 33.

The measuring arrangements, such as the measuring arrangements 50, 60 described above, may also employ other measuring techniques than ultrasound. Measuring techniques which may be employed may for instance include electro-magnetic techniques, gamma ray, and light (laser). Appropriate techniques suitable for measurement of fluid characteristics may be chosen by the person skilled in the art depending on the fluid that shall be characterized.

The invention claimed is:
1. A hydrocarbon production or processing fluid sampling assembly adapted to be installed with fluid communication with a flow of a fluid to be sampled, comprising:
   wherein the fluid sampling assembly comprises a rotating body supported in a chamber of a chamber housing, said chamber having a fluid inlet;
   wherein the fluid inlet is adapted to be arranged adjacent to and in fluid communication with said flow, thus being configured to receive a sample from the flow flowing past the hydrocarbon production or processing fluid sampling assembly;
   wherein the rotating body comprises a sample compartment with a sample compartment inlet;
   wherein the rotating body is connected to a rotation actuator;
   wherein the sample compartment is in fluid communication with the fluid inlet when the rotating body is in a rotational position where the sample compartment inlet is aligned with the fluid inlet;
   wherein the sample compartment is enclosed by an inner wall of the chamber and inner walls of the rotating body when the sample compartment inlet is in a position out of alignment with the fluid inlet;
   wherein the sample compartment inlet also constitutes a sample compartment outlet;
   wherein a portion of the inner wall of the chamber comprises a measuring arrangement adapted to measure fluid characteristic; and
   wherein the measuring arrangement is adapted to measure fluid characteristics of a fluid sample in the sample compartment at different vertical measuring positions within the fluid sample, when the rotating body is in a rotational position in which the sample compartment inlet is aligned with the measuring arrangement.

2. The hydrocarbon production or processing fluid sampling assembly according to claim 1, wherein the sample compartment inlet faces a direction crosswise to a rotation axis about which the rotating body is adapted to rotate.

3. The hydrocarbon production or processing fluid sampling assembly according to claim 1, wherein the sample compartment of the rotating body is in a through piston channel in which a reciprocating compartment piston is arranged, which compartment piston is adapted to reciprocate between respective end positions within the piston channel, wherein the rotating body comprises two sample compartment inlets of which one is arranged on respective sides of the reciprocating compartment piston, and that the chamber comprises a fluid outlet.

4. The hydrocarbon production or processing fluid sampling assembly according to claim 1, wherein the rotating body comprises two sample compartments which are divided by a fixed portion of the rotating body.

5. The hydrocarbon production or processing fluid sampling assembly according to claim 3, wherein the fluid outlet is connected to an outlet line which is connected to a sample bottle.

6. The hydrocarbon production or processing fluid sampling assembly according to claim 1, wherein the fluid outlet is connected to an outlet line which is in fluid communication with the fluid flow at a position downstream with respect to the fluid sampling assembly.

7. A method of taking a fluid sample from a hydrocarbon-containing fluid flow by using a fluid sampling assembly which is installed with fluid communication with said flow of fluid, the method comprising:
   a1) turning a rotating body within a chamber housing from a position in which a sample compartment inlet of a sample compartment in the rotating body is aligned with a fluid inlet of the chamber housing and positioned to let a fluid sample enter into the sample compartment through said sample compartment inlet, to a position in which the sample compartment inlet is not aligned with the fluid inlet, thereby encapsulating a fluid sample within said sample compartment;
   a2) then rotating the rotating body again, into a position where the fluid sample can exit the sample compartment through the sample compartment inlet, through which it entered;
   wherein the fluid inlet of the chamber housing is in fluid communication with said fluid flow; and
   b) performing measurement of fluid characteristic on a fluid sample in a first sample compartment with a measuring arrangement, wherein the first fluid sample compartment contains the fluid sample during measurement, while letting fluid from the fluid flow enter a second sample compartment.

8. The method according to claim 7, the method comprising:
   c) opening an outlet valve in an outlet line, thereby letting pressure in the fluid flow move a compartment piston along a piston channel within the rotating body, wherein a new fluid sample enters one sample compartment on one side of the compartment piston while a preceding fluid sample on the other side of the compartment piston leaves another sample compartment by being forced through the outlet line by said compartment piston.

9. The method according to claim 7, wherein the method comprising:
   d) between step a1) and step a2), when the rotating body is in the position in which the sample compartment inlet is not aligned with the fluid inlet, performing measurement of the fluid sample with a measuring arrangement; and
   wherein step a2) comprises turning the rotating body back to the position in which the sample compartment inlet of the sample compartment in the rotating body is aligned with the fluid inlet of the chamber housing, thereby replacing said fluid sample with a new fluid sample.

* * * * *